United States Patent [19]

Charrin et al.

[11] Patent Number: 6,080,814
[45] Date of Patent: Jun. 27, 2000

[54] POLYVINYL ALCOHOL PURIFICATION PROCESS

[75] Inventors: Jean-Jacques Charrin, Lyons; Françoie Vachet, Decines, both of France

[73] Assignee: Pardies Acetiques, Paris La Defense, France

[21] Appl. No.: 08/945,553

[22] PCT Filed: May 6, 1996

[86] PCT No.: PCT/FR96/00686

§ 371 Date: Nov. 4, 1997

§ 102(e) Date: Nov. 4, 1997

[87] PCT Pub. No.: WO94/34897

PCT Pub. Date: Nov. 7, 1996

[30] Foreign Application Priority Data

May 5, 1995 [FR] France ................................. 95 05893

[51] Int. Cl.⁷ ..................................... C08F 16/06
[52] U.S. Cl. ........................... 525/61; 528/480; 528/483; 528/503; 525/56

[58] Field of Search ..................... 525/61, 56; 528/480, 528/483, 503

[56] References Cited

U.S. PATENT DOCUMENTS

| | | | |
|---|---|---|---|
| 3,884,892 | 5/1975 | Winkler et al. | 525/62 |
| 5,030,404 | 7/1991 | Bonnebat et al. | 525/56 |

*Primary Examiner*—Judy M. Reddick
*Attorney, Agent, or Firm*—Dennison, Scheiner, Schultz & Wakeman

[57] ABSTRACT

A poly(vinyl alcohol) purification process is described, which includes heat treating a poly(vinyl alcohol) under agitation in an atmosphere unsaturated by water and with a water vapor mass content of 20 to 100%. The process of the invention may also include an additional drying step. A poly(vinyl alcohol) with an alcohol content, more particularly a methanol content, of lower than 1% and an ester content, more particularly a methyl acetate content, of lower than 1% is also described, which is provided in the form of flakes a few millimeters in size or of a powder with an average particle size advantageously higher than 600 μm.

10 Claims, No Drawings

POLYVINYL ALCOHOL PURIFICATION PROCESS

BACKGROUND OF THE INVENTION

The object of the present invention is a poly(vinyl alcohol) purification process, as well as a poly(vinyl alcohol) in the form of flakes of a few millimeters in size, or in the form of a powder whose average particle size of greater than 600 µm, and having low methanol and methyl acetate contents.

Poly(vinyl alcohol) is a polymer obtained by reaction of a poly(vinyl ester), generally poly(vinyl acetate), with an alcohol which can be ethanol, or, for an industrial use, methanol. The reaction is carried out with a catalyst which can be a basic catalyst such as sodium hydroxide, or even with an acidic catalyst such as sulphuric or hydrochloric acid. The basic catalyst is preferred for industrial use.

When the alcohol (called PVA in what follows) is prepared in a discontinuous manner, a polymer is obtained as a solid by precipitation in the alcohol used during an alcoholysis, and in the ester released during this same reaction; the precipitation generally takes place in a mixer. A step of neutralisation of the residual catalyst is then carried out, then a washing step of the polymer which is dried later.

When the process is carried out continuously, the product resulting from the reaction is first of all placed in the form of flakes mainly in the form of irregular flakes of 2 to 6 mm and of a thickness of a few tenths of millimeters, by means of a moist grinder, and a step of neutralisation of the residual catalyst is carried out, followed by a washing step. Upon completion of these operations, the polymer is separated as a solid which is dried by any known means. Once the product is dried, a grinding of the dried polymer is generally carried out.

Usually, it is noted that the particle size of the PVA particles obtained by the first process is finer, lower than 200 µm, than with the processes carried out continuously. In fact, by the continuous processes, the particle size of the particles after grinding is greater than 600 µm, even if a priori nothing prevents obtaining a finer particle size via this route. It is to be noted that particles having a larger size are interesting in this sense that they have better properties of use.

It is towards the above-mentioned drying steps that the present invention is directed. In fact, whatever the process used, the PVA resulting from the alcoholysis reaction contains a significant amount of solvents present during the reaction, such as the alcohol used and the ester released. Now, it is necessary to remove these solvents with a view to obtaining contents in the order of a few percent.

However, it is not possible to dry the PVA without precaution since this product is temperature-sensitive. In fact, if it is submitted to a high temperature, greater than or in the order of 100° C., for a significant period of time, it is noted then that some of its characteristics change, such as the water-solubility, the level of hydrolysis, the viscosity and the coloration, which is to be avoided.

A first obvious process for removing these solvents consists simply in heating the PVA at a temperature lower than that from which the polymer starts to degrade. However, such a process is not worthwhile since lowering the temperature leads to significantly increasing the drying time. Furthermore, this type of process does not allow sufficiently removing the alcohol present.

In order to solve this problem of effectiveness, without going to the detriment of the polymer's characteristics, it has been proposed to carry out the purification of the PVA by carrying out a heat treatment of the latter under an atmosphere having a relative humidity of at least 8%, more particularly lower than 15%. Thus, the drying is carried out at temperatures between 90 and 115° C., preferably under vacuum such that the speed of removal of the solvents is further accelerated, which is found to be in the order of a few hours.

However, this process seems more particularly suitable for the drying of PVA particles of small size. In fact, in this case, diffusion into the inside of the particles is facilitated with respect to particles of large size, and from this fact the removal of solvents is rendered easier. Thus, when this type of drying is carried out on a PVA obtained by a continuous process, with a relative humidity such as mentioned above, and at reduced pressure, the resulting PVA has a methanol content and an ester content of 1%.

Another more recently proposed process consists in mixing the PVA to be treated with liquid water in an amount of 10–30% by weight of water with respect to the polymer, such that a swelling of the particles is obtained. The particles are then submitted to a heat treatment in a vertical drier. The poly(vinyl alcohol) is introduced into the head of the drier and passes into a first zone surrounded by a double envelope heated with water. The temperature in this zone is one of the essential points of this process. It is in fact specified that if this temperature was too high, i. e. if the means of heating this zone was vapour and no longer water, the water would have evaporated before being able to act upon the polymer, as a result, the removal of the solvents would not be sufficient. After the passage into this first zone, the PVA is led into two other parts, heated by means of a double envelope comprising vapour, such that the water which is trapped in the polymer particles is evacuated.

This process is efficient but the operation time is a few hours, necessitating the implementation of a vertical drier. Furthermore, this process does not allow treating polymers comprising lower than 10% by weight of solvent with respect to the dry weight of PVA.

SUMMARY OF THE INVENTION

The object of the present invention is a poly(vinyl alcohol) purification process which is simple to carry out, economical and which can be furthermore rapid.

A further object of the present invention is a poly(vinyl alcohol) having very low solvent contents, and which are in the form of flakes whose sides measure at the most 10 mm, or in the form of a powder whose particle size is high.

Thus, the present invention consists in purifying a poly (vinyl alcohol) by submitting it to a heat treatment with agitation and under an atmosphere unsaturated by water and having a water vapour mass content between 20 and 100%.

The process according to the invention is particularly suitable for obtaining a PVA having an alcohol content of lower than 1% by weight with respect to the weight of moist PVA, as well as an ester content of lower than 1% with respect to the same reference. More particularly, the alcohol is methanol and the ester is methyl acetate.

Particularly advantageously, the present invention enables obtaining a PVA having an alcohol content of lower than 0.5% by weight with respect to the weight of moist PVA. Advantageously, the invention further enables obtaining a PVA with an ester content of lower than 0.5%.

Another object of the present invention is a poly(vinyl alcohol) in the form of flakes whose sides measure at the most 10 mm, and having an alcohol content, more particularly a methanol content, of lower than 1% and an ester content, more particularly a methyl acetate content, of lower than 1%, these values being expressed by weight with respect to moist PVA.

Another object of the present invention is a poly(vinyl alcohol) having an average particle size of greater than 600 μm and having an alcohol content, more particularly a methanol content, of lower than 1% and an ester content, more particularly a methyl acetate content, of lower than 1%, these values being expressed by weight with respect to moist PVA.

It has been found in a surprising way that the polymer treated under the conditions of the present invention, i. e. notably in the presence of high amounts of water, was not dissolved.

Furthermore, the process according to the invention allows purifying poly(vinyl alcohol) such that very low solvent contents be attained, in a treatment time which can be lower than an hour. Furthermore, this process does not necessitate the use of a particular apparatus.

However, other advantages and characteristics of the process according to the invention will become evident upon reading the description and Examples that follow.

DETAILED DESCRIPTION OF THE INVENTION

The PVA that can be treated by the process according to the invention can have any degree of polymerisation and/or level of alcoholysis.

The process according to the invention is particularly suitable for purifying PVA having an alcoholysis level of between 70 and 99%, more particularly between 95 and 99%.

Furthermore, the process of the invention enables treating the PVA directly resulting from the process, after neutralisation of the residual catalyst. It is even possible to treat, according to the invention, a PVA which is more or less dried by conventional processes. Thus, as an illustration, a PVA can be treated which has between 3 and 80% of solvents, expressed with respect to the weight of moist polymer.

The process according to the invention is suitable for purifying a PVA originating from preparative continuous or discontinuous methods. However, the process is particularly well adapted to drying PVA resulting from continuous processes, for which the problem of drying is more critical due to the significant size of the PVA particles to be dried.

According to a first characteristic of the process according to the invention, the treatment takes place in the presence of an atmosphere comprising water vapour and having a water vapour mass content of between 20 and 100%. "Water vapour content" is understood as meaning the ratio of the mass of water vapour and the total mass of water vapour and diluting gases.

More particularly, the water vapour mass content is between 40 and 100%. Preferably, the water vapour mass content is between 60 and 100%.

The atmosphere under which the process according to the invention is carried out comprises water vapour and optionally a diluting gas such as air, nitrogen or even any other gas inert towards PVA under the treatment conditions.

According to a second characteristic of the invention, the atmosphere is unsaturated by water. The saturation is defined as being the limit between a monophasic medium containing water vapour and a biphasic medium containing both water droplets and water vapour. This definition is valid for both pure water and for a mixture of water and a diluting gas.

The atmosphere under which the treatment according to the invention is carried out can approach saturation without however being attained.

According to a first variant, the treatment is carried out with water vapour and a diluting gas. In this case, the characteristics of temperature and pressure are selected such that the atmosphere has not attained the saturation limit.

According to a second variant, only water vapour is used. In this case, the vapour is superheated so as not to attain the saturation limit under the conditions of temperature and pressure.

According to another characteristic of the present invention, the operation takes place with agitation. More particularly, the agitation is such that the polymer is found in the form of a suspension in the gaseous atmosphere, whose particles are independent.

It is to be noted that it is important to minimise, even to prevent the condensation of water onto the PVA particles, such that a partial solubilisation of the PVA is prevented which could lead to the particles sticking together, rendering the particles useless for what follows.

Furthermore, the agitation must preferably be sufficient in order to enable a good solid-gas contact, so as to optimally get rid of the solvents concerned.

The condensation of a film of water on the particles of PVA can even be prevented by controlling the temperature of the PVA at the start of the treatment. Thus, the temperature of the product at the start of the treatment is more particularly around the dew point of the treatment atmosphere. Preferably, this temperature is higher than the dew point of the treatment atmosphere.

Furthermore, it is to be noted that in order to prevent any problem of degradation of the polymer, it is preferable that the temperature of the PVA does not go over 130° C. during the treatment.

According to a variant of the invention, the amount of water vapour coming into contact with the PVA (heated as indicated before) during the treatment is between 0.2 and 0.8 kg per kilogram of dry PVA. Preferably, this amount is between 0.4 and 0.6 kg with respect to the same reference.

The process according to the invention can therefore take place in any type of apparatus known to the person skilled in the art which comprises mechanical means of mechanical agitation. Apparatuses can even be used in which the agitation is carried out by means of a gas flow, as is the case notably for fluidised beds, transported beds or even jet beds.

More particularly, the treatment according to the invention is carried out with agitation for which the Froude number is between 0.04 and 3, and preferably between 0.06 and 2.5.

It is recalled that the Froude number corresponds to the following ratio:

$$(\pi.N)^2.D/g$$

in which formula N represents the number of turns per second, D the diameter of the stirrer and g the acceleration due to gravity.

The time of the process according to the invention is advantageously reduced with respect to known prior processes since it is possible to obtain the solvent contents desired in a treatment time as short as a quarter of an hour to an hour. Of course, longer times are not excluded.

In fact, the treatment time can be adapted very advantageously, with the type of apparatus that is used for drying the PVA.

Thus, according to a first particularly advantageous variant of the present invention, the PVA treatment time is between a quarter of an hour and 2 hours, more particularly between half an hour and an hour. According to this variant, the drying is carried out with a stronger agitation, i. e. corresponding to a Froude number between 0.5 and 3, and preferably between 0.5 and 2.5.

Furthermore, the unsaturated water vapour introduction flow rate is such that the amount of vapour placed in contact with the heated product is between 0.2 and 0.8 kg per kilogram of dry PVA, and preferably between 0.4 and 0.6 kg with respect to the same reference.

According to a second variant of the present invention, the PVA treatment is carried out for a longer time, 2 to 4 hours for example. In this case, the treatment according to the invention can be carried out with a weaker agitation, i. e. corresponding to a Froude number between 0.04 and 0.5, preferably between 0.06 and 0.5.

The unsaturated water vapour introduction flow rate is determined by the person skilled in the art such that the amount of vapour placed in contact with the heated product be between 0.2 and 0.8 kg per kilogram of dry PVA, and preferably between 0.4 and 0.6 kg with respect to the same reference.

The pressure at which the operation is carried out is at least 0.5 absolute bar. More particularly, it is between 0.5 and 6 absolute bar. Advantageously, the pressure is between 0.8 and 3 absolute bar.

Advantageously, the pressure at which the treatment is carried out is around atmospheric pressure.

The temperature of the entry of the gases during this step is between 80 and 350° C. and depends upon the heating means used.

The heating of the medium during the pre-heating of the PVA or during the introduction of the water vapour can be done by any known means.

Thus, a heating of the conductive type can be carried out, by using an apparatus comprising a double envelope. A convective type heating can also be carried out by means of a hot gas which will advantageously be the atmosphere under which the treatment is carried out. These two means of heating can even be combined.

According to a particularly advantageous variant of the present invention, a second step can be carried out which consists in submitting the resulting PVA to a additional heat treatment essentially intended to remove the water present in the PVA from the first step. It is to be noted that this operation further allows even removing a few traces of solvents.

This conventional drying operation can be carried out by any means known to the person skilled in the art. Thus, a conductive drying can be carried out under vacuum or at atmospheric pressure. This step can even be carried out by a convective drying by means of a hot gas. This hot gas can be selected from superheated water vapour and/or any other gas inert towards PVA.

This operation can be carried out in a fluidised bed or a crossed bed.

As has been indicated before, the drying process according to the invention allows decreasing the contents of the solvents, the alcohol and the ester, present in the PVA, without observing degradation of the quality of the PVA.

Thus, the PVA obtained according to the process according to the invention has an alcohol content of lower than 1% by weight with respect to the weight of moist PVA, as well as an ester content of lower than 1% with respect to the same reference. More particularly, the alcohol is methanol and the ester is methyl acetate.

Particularly advantageously, the present invention allows obtaining a PVA having an alcohol content of lower than 0.5% by weight with respect to the moist PVA. The present invention also allows obtaining, advantageously, a PVA with an ester content of lower than 0.5%.

It is to be noted that according to the quality of the PVA treated, i. e. notably, according to its degree of drying before the treatment of the invention, the ratio, expressed by weight, of alcohol to ester is between 1 and 20. More particularly, said ratio is between 1 and 10, and preferably between 1 and 5.

The object of the present invention is a poly(vinyl alcohol) in the form of flakes whose sides measure at the most 10 mm and having an alcohol content, more particularly a methanol content, of lower than 1% and an ester content, more particularly a methyl acetate content, of lower than 1%, these values being expressed by weight with respect to moist PVA.

The PVA flakes more particularly originate from the continuous PVA synthetic process and have been the subject of the drying treatment according to the invention.

The dimensions of the sides are more particularly greater than 1 mm and at the most 10 mm. Preferably, the dimension of the sides is between 2 and 5 mm. The thickness of the flakes is in the order of 0.05 to 0.3 mm, preferably in the order of 0.1 to 0.2 mm.

Finally, the object of the present invention is a poly(vinyl alcohol) whose average particle size is greater than 600 $\mu$m and having an alcohol content, more particularly a methanol content, of lower than 1% and an ester content, more particularly a methyl acetate content, of lower than 1%, these values being expressed by weight with respect to moist PVA.

More particularly, the PVA according to the invention has an average particle size between 600 and 1000 $\mu$m, preferably the average particle size is between 700 and 900 $\mu$m.

It is to be noted than the PVA described above can notably be obtained by grinding, by any means known to the person skilled in the art, of the flakes of PVA which have been described before.

According to an advantageous variant of the invention, the PVA, whether it is in the form of flakes or in the form of a powder whose particle size is greater than 600 $\mu$m, has a methanol content of lower than 0.5%, and a methyl acetate content of lower than 0.5%, contents expressed by weight with respect to the weight of moist PVA.

What has been said about the poly(vinyl alcohol), and notably about the level of alcoholysis, remains valid.

Moreover, the PVA according to the invention has a coloration close to that of he product originating from the synthesis. Non-limiting examples of the present invention are now given.

EXAMPLE 1

This example illustrates a process of purifying PVA in two successive steps; the first being carried out in the presence of diluted water vapour.

The apparatus in which the treatment according to the invention is carried out (turbosphere Moritz®), comprises a rounded tank of maximal working capacity of 6 liters, externally heated by a double envelope run through with water vapour at 130° C.

The envelope is equipped with an agitation means having the same form, for the main part of the working volume, as that of the tank, giving the PVA flakes a significant mixing movement.

The nitrogen and the water vapour can be introduced via the upper lid with controlled flow rates.

The analyses of the methanol content and the methyl acetate content are done by "head space" chromatography. The determination of the water content is done by means of a Karl-Fischer Metrohm® apparatus with oven.

1489 g of PVA flakes comprising 28% methanol and 30.4% methyl acetate are loaded into the heated apparatus described above.

The water vapour flow rate at atmospheric pressure is 420 g/h and the nitrogen flow rate is 190 g/h.

The water mass content of the atmosphere is therefore 69% for a temperature around 95° C.

The Froude number is 1.4.

The pressure is 1020 mbar.

The temperature of the polymer rose from an initial plateau towards 80° C. up to 107° C. after one hour of introduction of vapour and nitrogen.

After one hour of treatment, the product is dried, in a second step, by conduction through the walls of the apparatus. The flow rate of nitrogen is maintained at the same flow rate as before.

The operation is conducted for one hour.

The pressure is 1020 mbar.

Upon completion of the drying step, the product is in the form of individual and brittle flakes of very light ivory colour.

The product is ground to 800 µm and has the same contents of methanol, methyl acetate and water as the flakes.

The results are grouped in the Table below:

| time (minutes) | methanol (weight %) | methyl acetate (weight %) | water (weight %) |
| --- | --- | --- | --- |
| 0 | 28 | 30.4 | — |
| 60 | 0.65 | 0.76 | 4.5 |
| 120 | 0.39 | 0.75 | 0.95 |

The contents in weight % are expressed with respect to the weight of moist PVA.

EXAMPLE 2

This example illustrates a process of treating PVA in two successive steps the first of which is carried out in the presence of slightly superheated pure water vapour.

The treatment is carried out in the same apparatus as that described in Example 1.

1500 g of PVA comprising 16.2% methanol and 1.4% methyl acetate are introduced into the heated apparatus.

The pure water vapour (water mass content of 100%) is introduced with a flow rate of 1600 g/h at a temperature around 102° C. for 40 minutes.

The operation is carried out under a pressure of 1020 mbar.

The Froude number is 2.1.

The apparatus is then placed under vacuum of 100 mbar for one hour.

The temperature of the product rises from 85 to 107° C. during the treatment of the water vapour attaining 105° C. at the end of the drying.

The results obtained are grouped in the following Table:

| time (minutes) | methanol (weight %) | methyl acetate (weight %) | water (weight %) |
| --- | --- | --- | --- |
| 0 | 16.2 | 1.4 | — |
| 30 | 0.4 | 0.07 | 10.2 |
| 40 | 0.08 | 0.01 | 12.8 |
| 100 | 0.03 | 0.03 | 0.32 |

It is noticed that as soon as 30 minutes, the treatment with the water vapour allows attaining a methanol content and a methyl acetate content of lower than 0.5%. Despite the water content being 12.8% before starting the drying step, the PVA resulting from the process according to the invention is in the form of individual and dry particles.

The final product is constituted of individual flakes of very light ivory colour.

The product was ground to 800 µm and has the same contents of methanol, methyl acetate and water as the flakes.

EXAMPLE 3

This example illustrates a one-step process in the presence of diluted water vapour.

881 g of PVA titrating 5.1% methanol and 0.73% methyl acetate are introduced into the hot apparatus described in Example 1.

A mixture of gases having a water mass content of 69% and comprising 190 g/h of nitrogen and 420 g/h of water vapour, is introduced at atmospheric pressure and at a temperature in the order of 95° C. for 3 hours.

The temperature of the product attains 112° C. at the end of the step.

The Froude number is 2.1.
The results are grouped in the Table below:

| time (minutes) | methanol (weight %) | methyl acetate (weight %) | water (weight %) |
| --- | --- | --- | --- |
| 0 | 5.1 | 0.73 | — |
| 30 | 1.46 | 0.46 | — |
| 60 | 0.55 | 0.27 | 2 |
| 90 | 0.42 | 0.28 | |
| 120 | 0.29 | 0.22 | 1.9 |
| 180 | 0.18 | 0.20 | 1.8 |

The product is in the form of dry, brittle flakes and keep their initial colour.

The product was ground to 800 µm and has the same contents of methanol, methyl acetate and water as the flakes.

COMPARATIVE EXAMPLE 4

This example consists in carrying out a treatment in the presence of water vapour under reduced pressure.

962 g of PVA comprising 5.1% methanol and 2.1% methyl acetate are loaded into the hot apparatus described in Example 1.

Water vapour is introduced with a flow rate of 300 g/h to a temperature of 102° C. (mass content of 100%) at a pressure of 300 absolute mbar for 95 minutes.

The Froude number is 2.1.

The temperature of the product rises to 105° C. attaining a stable value of 114° C.

The following Table groups the results obtained:

| time (minutes) | methanol (weight %) | methyl acetate (weight %) | water (weight %) |
|---|---|---|---|
| 0 | 5.1 | 2.1 | — |
| 5 | 4.48 | 2.02 | 1.96 |
| 65 | 1.44 | 1.49 | 0.64 |
| 95 | 1.12 | 1.47 | 0.48 |

Despite a vapour treatment of 95 minutes, the residual contents of these two solvents are greater than 1%, when such conditions are put into operation.

The flakes obtained are dry and brittle.

The product was ground to 800 μm and has the same contents of methanol, methyl acetate and water as the flakes.

COMPARATIVE EXAMPLE 5

The object of this example is a conventional type drying.

1538 g of PVA comprising 28% methanol and 30.4% methyl acetate are loaded into the hot apparatus.

190 g/h of nitrogen (water mass content of 0) under atmospheric pressure (1020 mbar) are used throughout the test.

The Froude number is 1.4.

The temperature of the product rises from 82° C. to 110C.

The following Table groups the results obtained:

| time (minutes) | methanol (weight %) | methyl acetate (weight %) |
|---|---|---|
| 0 | 28 | 30.4 |
| 30 | 10.35 | 2.64 |
| 60 | 3.05 | 2.54 |
| 120 | 1.39 | 2.43 |

It is noted that despite a treatment time of 2 hours, the methanol content and the methyl acetate content remain greater than 1%.

The product was ground to 800 μm and has the same contents in methanol, methyl acetate and water as the flakes. Furthermore, and in contrast to what is observed when the process according to the invention is carried out, a variation in the coloration of the treated PVA is noted, which goes from light ivory to amber-yellow.

What is claimed is:

1. In a process for purification of poly(vinyl alcohol) obtained by a reaction of a poly(vinyl ester) with an alcohol with release of an ester, the improvement comprising subjecting said poly(vinyl alcohol) to a heat treatment with agitation and under an atmosphere having a water vapor content between 20 and 100 wt % and which is not saturated with water, to obtain a poly(vinyl alcohol) having a content of said alcohol of less than 1 wt % and a content of said ester of less than 1 wt %, with respect to moist poly(vinyl alcohol).

2. According to the process claim 1, wherein the treatment is carried out under an atmosphere having a water vapour content between 40 and 100 wt %.

3. The process according to claim 1, wherein the treatment is carried out under an atmosphere further comprising a diluting gas.

4. The process according to claim 3, wherein the diluting gas is nitrogen, air or any other gas inert towards poly(vinyl alcohol) under treatment conditions.

5. The process according to claim 1, wherein the treatment is carried out under an atmosphere of superheated pure water vapour.

6. The process according to claim 1, wherein the treatment is carried out with a gas entry temperature between 80 and 350° C.

7. The process according to claim 1, wherein the treatment is carried out with a poly(vinyl alcohol) having, at the start of treatment, a temperature around the dew point of the treatment atmosphere.

8. The process according to claim 1, wherein the treatment is carried out with an amount of water vapor coming into contact with the poly(vinyl alcohol) during the treatment of between 0.2 and 0.8 kg per kilogram of dry poly(vinyl alcohol).

9. The process according to claim 7, wherein the treatment is carried out at a pressure of at least 0.5 absolute bar.

10. The process according to, claim 1, further comprising subjecting the poly(vinyl alcohol) obtained to an additional heat drying treatment.

* * * * *

UNITED STATES PATENT AND TRADEMARK OFFICE
CERTIFICATE OF CORRECTION

PATENT NO. : 6,080,814
DATED : June 27, 2000
INVENTOR(S) : JEAN-JACQUES CHARRIN et al It is certified that error appears in the above-indentified patent and that said Letters Patent is hereby corrected as shown below:

Title page, after [75] Inventors:

line 1, change "Lyons" to --Lyon--;

line 2, change "Françoie" to --François--.

After [87] PCT Pub. No.: change "WO 94/34897" to

--WO 96/34897--.

Signed and Sealed this

Eighth Day of May, 2001

Attest:

NICHOLAS P. GODICI

*Attesting Officer*   *Acting Director of the United States Patent and Trademark Office*